(12) United States Patent
Navar et al.

(10) Patent No.: US 10,011,762 B2
(45) Date of Patent: Jul. 3, 2018

(54) BIOCIDAL COMPOSITION

(71) Applicant: HighQ Services, LLC, Cedar Park, TX (US)

(72) Inventors: Fermin Navar, Austin, TX (US); Babak Samani, Cedar Partk, TX (US)

(73) Assignee: HighQ Services, LLC, Cedar Park, TX (US)

( * ) Notice: Subject to any disclaimer, the term of this patent is extended or adjusted under 35 U.S.C. 154(b) by 37 days.

(21) Appl. No.: 15/202,474

(22) Filed: Jul. 5, 2016

(65) Prior Publication Data

US 2017/0002260 A1    Jan. 5, 2017

Related U.S. Application Data

(60) Provisional application No. 62/188,546, filed on Jul. 3, 2015.

(51) Int. Cl.
| | |
|---|---|
| *C09K 8/60* | (2006.01) |
| *C09K 8/68* | (2006.01) |
| *A01N 35/04* | (2006.01) |
| *A01N 33/12* | (2006.01) |
| *A01N 43/80* | (2006.01) |
| *A01N 31/02* | (2006.01) |
| *A01N 59/06* | (2006.01) |

(52) U.S. Cl.
CPC .............. *C09K 8/605* (2013.01); *A01N 31/02* (2013.01); *A01N 33/12* (2013.01); *A01N 35/04* (2013.01); *A01N 43/80* (2013.01); *A01N 59/06* (2013.01); *C09K 8/68* (2013.01); *C09K 2208/20* (2013.01); *C09K 2208/32* (2013.01)

(58) Field of Classification Search
CPC ........ A01N 31/02; A01N 33/12; A01N 35/04; A01N 43/80; A01N 59/06; C09K 8/605; C09K 8/68; C09K 2208/20; C09K 2208/32
See application file for complete search history.

(56) References Cited

U.S. PATENT DOCUMENTS

2013/0029884 A1* 1/2013 Malchesky ............ A01N 31/08
                                                                 507/219

* cited by examiner

*Primary Examiner* — Michael B. Pallay

(57) ABSTRACT

A biocidal composition includes glutaraldehyde, alkyl-based quaternary ammonium, benzyl-containing quaternary ammonium, and an isothiazolinone composition. The biocidal composition can further include water, alcohol, or a magnesium salt. Such a biocidal composition finds particular use in treating fracking fluids. The biocidal composition can be mixed with a treatment fluid prior to pumping the treatment fluid through a well head.

20 Claims, 2 Drawing Sheets

TABLE 1.
Results of Microbial Growth Tests to Evaluate Biocide Treated Samples

| Biocide | Exposure Time | GHB | APB | SRB |
|---|---|---|---|---|
| No biocide control | none | $4.5 \times 10^3$ | $4.5 \times 10^3$ | $2.5 \times 10^3$ |
| Biocide A/Control | 1 minute | 0 of 6 | 0 of 6 | 5 of 6 (last 5 dilutions) |
| Biocide A/Control | 2 minutes | 2 of 6 (dilutions 5 + 6) | 2 of 6 (dilutions 5 + 6) | 5 of 6 (last 5 dilutions) |
| Biocide A/Control | 3 minutes | 0 of 6 | 0 of 6 | 5 of 6 (last 5 dilutions) |
| Biocide A/Control | 4 minutes | 0 of 6 | 0 of 6 | 5 of 6 (last 5 dilutions) |
| Biocide A/Control | 5 minutes | 0 of 6 | 0 of 6 | 5 of 6 (last 5 dilutions) |
| Biocide B/#103 | 1 minute | 1 of 6 ($4^{th}$ dilution) | 1 of 6 ($4^{th}$ dilution) | 5 of 6 (last 5 dilutions) |
| Biocide B/#103 | 2 minutes | 1 of 6 ($5^{th}$ dilution) | 1 of 6 ($5^{th}$ dilution) | 5 of 6 (last 5 dilutions) |
| Biocide B/#103 | 3 minutes | 0 of 6 | 0 of 6 | 5 of 6 (last 5 dilutions) |
| Biocide B/#103 | 4 minutes | 0 of 6 | 0 of 6 | 5 of 6 (last 5 dilutions) |
| Biocide B/#103 | 5 minutes | 0 of 6 | 0 of 6 | 5 of 6 (last 5 dilutions) |
| Biocide C/#104 | 1 minute | 2 of 6 (dilutions 3 + 4) | 2 of 6 (dilutions 3 + 4) | 5 of 6 (last 5 dilutions) |
| Biocide C/#104 | 2 minutes | 0 of 6 | 0 of 6 | 5 of 6 (last 5 dilutions) |
| Biocide C/#104 | 3 minutes | 1 of 6 ($4^{th}$ dilution) | 1 of 6 ($4^{th}$ dilution) | 5 of 6 (last 5 dilutions) |
| Biocide C/#104 | 4 minutes | 0 of 6 | 0 of 6 | 5 of 6 (last 5 dilutions) |
| Biocide C/#104 | 5 minutes | 0 of 6 | 0 of 6 | 5 of 6 (last 5 dilutions) |

FIG. 3

BIOCIDAL COMPOSITION

CROSS-REFERENCE TO RELATED APPLICATION(S)

This application claims benefit of U.S. Provisional Application No. 62/188,546, filed Jul. 3, 2015, which is incorporated herein by reference in its entirety.

FIELD OF THE DISCLOSURE

This disclosure, in general, relates to biocidal compositions, particularly biocidal compositions useful in well treatments, and methods for using such biocidal compositions.

BACKGROUND

Fluid production, such as oil and gas production or water production, from subterranean reservoirs often relies upon well treatments to enhance current and continuous production of the desired fluid. With increasing interest in non-traditional subterranean strata, such as oil or gas shales, there has been an increased interest in well treatments, such as fracking. In general, well treatments, including fracking and hot oil treatments, utilize pressured flow of liquids down a well. During such treatments, there is a risk of biological contamination of subterranean strata exposed to the treatment fluids.

Bacteria can have costly impact by restricting production and or leading to corrosion failures and potential environmental consequences in the field. The metabolic byproduct hydrogen sulfide from certain pervasive bacteria types also can pose a serious health and safety risk to oilfield workers and nearby communities. In particular, the watery fluids used to fracture rocks heat up due to high pressure when such fluids are pumped into the ground at high speed, causing bacteria and mold to multiply. Under such conditions, bacteria can grow and thus, inhibit the flow and quality of gas or oil, corrode well casings, limit efficacy of oil and gas extraction, and produce highly toxic hydrogen sulfide gas.

As such, an improved biocidal composition, particularly for use in such well treatment fluids, would be desirable.

SUMMARY

In an example, a biocidal composition includes glutaraldehyde, alkyl-based quaternary ammonium, benzyl-containing quaternary ammonium, and an isothiazolinone composition. The biocidal composition can further include water, alcohol, or an alkaline earth metal salt. In an example, such a biocidal composition finds particular use in treating fracking fluids. The biocidal composition can be mixed with a treatment fluid prior to pumping the treatment fluid through a well head.

BRIEF DESCRIPTION OF THE DRAWINGS

The present disclosure may be better understood, and its numerous features and advantages made apparent to those skilled in the art by referencing the accompanying drawings.

FIG. 3 includes a Table 1 of the Example.

The use of the same reference symbols in different drawings indicates similar or identical items.

DETAILED DESCRIPTION

Figure 1:
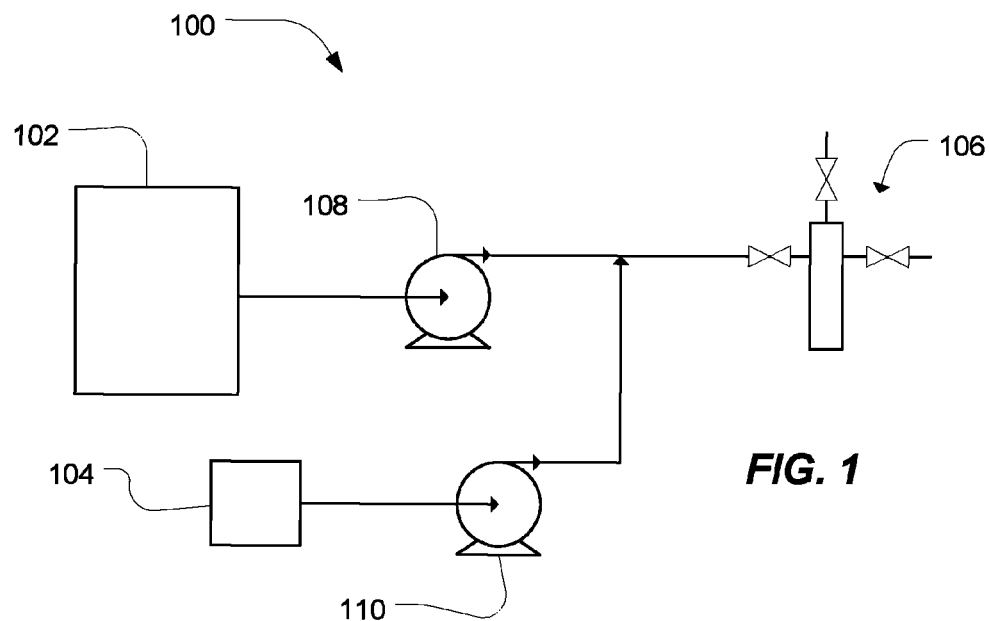
FIG. 1 includes an illustration of an exemplary treatment system.

In an exemplary embodiment, a biocidal composition includes glutaraldehyde, an alkyl-based quaternary ammonium, a benzyl-containing quaternary ammonium, and an isothiazolinone composition. The biocidal composition can be an aqueous solution and can further include water. In a further example, the biocidal composition can include alcohol or an alkaline earth metal salt. In an example, the alkyl-based quaternary ammonium includes a dialkyl dimethyl ammonium salt. In a further example, the benzyl-containing quaternary ammonium can include an alkyl benzyl dimethyl ammonium salt. The isothiazolinone composition can include a methyl isothiazolinone compound, a methyl chloro isothiazolinone compound, or a combination thereof. In another example, the alcohol can be methanol, ethanol, propanol, isopropyl alcohol, or a combination thereof. The alkaline earth metal salt can include magnesium nitrate or magnesium chloride.

In use, the biocidal composition can be mixed with a well treatment fluid as the well treatment fluid is pumped into the well. For example, the well treatment fluid can be pumped through pipes to a well and then down the well head or wellbore. A biocidal composition can be injected into the well treatment fluid as it is being pumped into the well head and down the wellbore prior to the treatment fluid entering the well head. In particular, the biocidal composition can be that described herein.

In an example, the biocide composition is an aqueous composition and includes water. For example, the biocidal composition can include 0.1% to 60% water by weight, such as 0.1% to 50%, or 5% to 40% water by weight. Alternatively, the biocidal composition can be free of water.

In particular example, the biocidal composition includes glutaraldehyde in an amount of 0.5% to 35% by weight, such as 5% to 35%. For example, the glutaraldehyde can be included in amount of 10% to 20%, such as an amount of 15% to 28% or an amount of 23% to 28% by weight.

The biocide composition can also include alkyl-based quaternary ammonium. For example, the alkyl-based quaternary ammonium can be a dialkyl dimethyl ammonium salt. Such a salt can include a halogen salt, such as a chloride, iodide, or fluoride salt, or a nitrate salt, a sulfate salt, or a combination thereof. For example, the alkyl group of the dialkyl moiety of the dialkyl dimethyl ammonium salt can include 8 to 18 carbons. For example, the alkyl group can have 8 to 14 carbons, such as 10 to 12 carbons. In an example, the alkyl-based quaternary ammonium salt includes didecyl dimethyl ammonium chloride. The alkyl-based quaternary ammonium salt can be included in the biocidal composition in amount of 0.5% to 15% by weight, such as 5% to 15%. For example, the alkyl-base quaternary ammonium salt can be included in amount of 5% to 10%, such as 6% to 8% by weight.

In a further example, the biocidal composition includes a benzyl-containing quaternary ammonium, such as an alkyl benzyl dialkyl ammonium salt. Such a salt can include a halogen salt, such as a chloride, iodide, or fluoride salt, or a nitrate salt, a sulfate salt, or a combination thereof. The alkyl moiety of the alkyl benzyl dialkyl ammonium salt can have 8 to 18 carbons. For example, the alkyl moiety can have 8 to 14 carbons, such as 8 to 12 carbons, or 10 to 12 carbons. The dialkyl moiety of the alkyl benzyl dialkyl ammonium salt can be a dimethyl or diethyl moiety, or a combination thereof. In particular, the dialkyl moiety of the alkyl benzyl dialkyl ammonium salt is dimethyl. For example, the benzyl-containing quaternary ammonium can include dodecyl benzyl dimethyl ammonium chloride. The benzyl-containing quaternary ammonium can be included in the biocidal composition in an amount of 0.1% to 25% by weight, such as 1% to 25%. For example, the benzyl-containing quaternary ammonium can be included in an amount of 2% to 20%, such as an amount of 2% to 15% or an amount of 3% to 9% by weight.

The biocidal composition can also include an isothiazolinone composition. An exemplary isothiazolinone composition includes a methyl isothiazolinone or methyl chloro isothiazolinone compound, or a combination thereof. The isothiazolinone composition can be included in an amount of 0.0005% to 5%, such as an amount of 0.0005% to 1% or an amount of 0.001% to 1% by weight.

Optionally, the biocidal composition can further include alcohol. An exemplary alcohol includes methanol, ethanol, propanol, isopropyl alcohol, or a combination thereof. In a particular example, the alcohol includes ethanol. The alcohol can be included in the biocidal composition in amounts of 0.1% to 10% by weight. For example, the alcohol can be included in an amount of 0.5% to 5%, such as an amount of 0.5% to 4% or an amount of 1.5% to 3% by weight.

The biocidal composition can further include an alkaline or alkaline earth metal salt. For example, the biocidal composition can include an alkaline earth metal salt, such as a magnesium salt. An exemplary magnesium salt includes magnesium chloride, magnesium nitrate, or combination thereof. The salt can be included in the biocidal composition in an amount of 0.5% to 10%, such as an amount of 0.5% to 5% by weight.

In an additional example, the biocidal composition can also optionally include beta-glucan. For example, the biocidal composition can include beta-glucan in an amount of 0.01% to 10% by weight, such as an amount of 0.01% to 5%, an amount of 0.01% to 1.0%, an amount of 0.01% to 0.5%, or an amount of 0.01% to 0.1%.

In an additional example, the biocidal composition can also optionally include 2-bromo-2-nitropropane-1,3-diol. For example, the biocidal composition can include 2-bromo-2-nitropropane-1,3-diol in an amount of 0.01% to 10% by weight, such as an amount of 0.01% to 5%, an amount of 0.01% to 1.0%, an amount of 0.01% to 0.5%, or an amount of 0.01% to 0.1%.

In particular, a fast acting biocidal composition at dilution has been found to consist essentially of glutaraldehyde in an amount of 5% to 35%, alkyl-based quaternary ammonium in an amount of 5% to 15%, benzyl-containing quaternary ammonium in an amount of 1% to 25%, an isothiazolinone composition in an amount of 0.0001% to 20%, and alcohol in an amount of 0.1% to 10%, each of the percentages being expressed by weight.

In a particular embodiment, the biocidal composition useful as a fracking fluid additive consists of water, glutaraldehyde in an amount of 5% to 35%, alky-based quaternary ammonium in an amount of 5% to 15%, benzyl-containing quaternary ammonium an amount of 1% to 25%, alcohol in an amount of 0.1% to 10%, an isothiazolinone composition in an amount of 0.0001% to 20%, and magnesium salt in an amount of 0.1% to 20%, each of the percentages being expressed by weight.

Such biocidal compositions find particular use in providing biocidal properties to treatment fluids for use in treating a well. Such biocidal compositions can be added to treatment fluids prior to injecting the treatment fluids into a well and into a geological structure or strata. For example, FIG. 1 includes an illustration of an exemplary system 100 for treating geological strata through a well. A treatment fluid container 102 feeds a treatment fluid to a well head 106 through a pump 108. Exemplary treatment fluid includes fracking fluids, hot oil treatments, or other fluids useful in treating wells and geological strata associated therewith.

A biocidal composition container 104 can include a biocidal composition that is pumped using a pump 110 to mix with the treatment fluid prior to the treatment fluid entering the well head 106.

In another example, the biocide can be added to the fluid container 102 prior to pumping the fluid. Other treatment components, such as sand or ceramic particulate, can be added to the treatment fluid prior to the treatment fluid being pumped into the well head.

Figure 2:
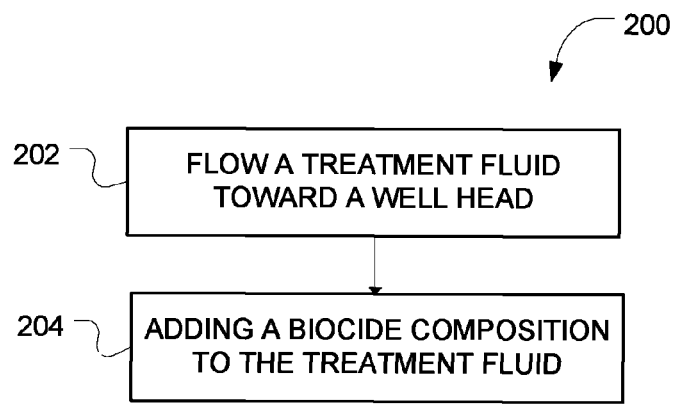
FIG. 2 includes a flow diagram illustrating an exemplary method.

Using the above described fast acting biocidal composition, biological contamination can be eradicated quickly, reducing the risk of contamination of the well and geological structure. For example, as illustrated in FIG. 2, a method 200 includes flowing a treatment fluid towards a well head, as illustrated at 202. Exemplary treatment fluid can include a fracking fluid, hot oil treatment fluid, or other fluids useful in treating wells and geological structures associated with the wells. Prior to the treatment fluid entering a well head, a biocidal composition can be mixed with the treatment fluid, as illustrated at 204. Using the fast acting biocidal compositions described herein, the treatment fluid can be treated close to the well head and down the well with limited risk of contaminating geological structures or strata with biological contaminants.

In another example, the biocidal composition can be added to a portion of the treatment fluid (e.g., to water) prior to other components. For example, the biocidal composition can be added to the water prior to pumping the water, and the other components, such as sand or ceramic particulate, can be added prior to injection into the well head.

In particular, using the above described biocidal compositions during well treatments can increase your production, prevent injector plugging, lower your health, safety and environmental risks, and prevent bacterial proliferation

EXAMPLE

Biocidal compositions are tested for efficacy at dilution. Three biocide samples are tested to determine the effectiveness of the biocides to kill planktonic bacterial cells typically found in oil and gas industry environments. The Biocide A/control includes water, glutaraldehyde, quaternary ammonium chloride, alkyl dimethyl benzyl ammonium chloride, and ethanol Biocide B includes water, glutaraldehyde, dialkyl dimethyl ammonium chloride, alkyl benzyl dimethyl ammonium chloride, methyl isothiazolinone, methyl chloro isothiazolinone, and ethanol Biocide C includes water, glutaraldehyde, dialkyl dimethyl ammonium chloride, alkyl benzyl dimethyl ammonium chloride, and ethanol. The biocides are tested against a mixed microbial culture derived from oilfield samples and consisting of predominantly corrosion associated bacteria Sulfate Reducing Bacteria (SRB) and Acid Producing Bacteria (APB), and General Heterotrophic Bacteria (GHB). The mixed microbial community is then used in biocide testing employing each of the three biocides at one concentration (0.025% that is equivalent to 250 ppm) and five exposure times (1, 2, 3, 4, and 5 minutes). The concentration of bacteria in the biocide-free control is determined using triplicate dilution series in microbial growth medium for the cultivation of oilfield bacteria as specified in NACE Standard TM0194. The concentration of bacteria in the biocide containing samples is also determined using microbial growth media, but only single dilution series are employed. After the inoculation of microbial growth medium, the medium is incubated at 30° C. for 14 days.

Microbial growth tests quantify bacterial populations by inoculating dilution series to determine what amount of dilution is required to achieve no growth when the media is incubated. Six ten-fold dilutions are employed to determine the concentration of bacteria that survived exposure to biocides. The biocide-free control sample contained $4.5 \times 10^5$ APB cells/mL and $2.5 \times 10^6$ SRB cells/mL. Therefore, if the culture is used to inoculate single dilution series consisting of six ten-fold dilutions, it is expected that growth will be obtained in all six dilutions in APB media and all six dilutions in SRB media. Additional dilution of the biocide-free culture results in no growth.

The determination of the concentration of bacteria in biocide-containing samples is complicated by the presence of biocide that is progressively diluted along with the bacterial cells. In other words, the biocide-containing samples start with 250 ppm biocide and when they are used to inoculate dilution series in microbial growth tests the first dilution contains 25 ppm biocide plus surviving bacteria, the second dilution contains 2.5 ppm biocide plus surviving bacteria, and so on. For this reason, it is common that the first one or two vials in a dilution series from a biocide test may fail to show growth because of residual biocide, particularly when short exposure times are tested, but subsequent vials in the dilution series will show growth because the residual biocide has been diluted to a concentration that is not capable of killing bacteria.

Diluted biocidal compositions are applied to plates exposed to various biological contaminants. Plates are observed for a number of colonies growing following a period of exposure as shown in Table 1. (FIG. 3). The data reported in Table 1 are after 14 days of incubation at 30° C. The recommended incubation period for GHB/APB media is 14 days, while for SRB, the recommended incubation period is 28 days. The results are reported as final after only 14 days incubation because the SRB grew in the last 5 of the 6 dilution vials in all samples. Therefore, longer incubation time will not change these results. Based on the data, all three biocides are highly effective in killing GHB and APB at 250 ppm with exposure times as short as one minute, but none of the three biocides appear to be effective in killing SRB at 250 ppm with an exposure time of 1 to 5 minutes. The reason that only the last five dilutions show growth of SRB while the first dilution does not, is because the first dilution contains 25 ppm biocide and apparently this is sufficient to kill SRB when a prolonged exposure time is used. When the data for the survival of GHB and APB are examined, there is no growth detected in any of the three biocides when exposure times of 4 or 5 minutes are used. There is limited growth of GHB/APB detected at exposure times of from 1 to 3 minutes.

As illustrated in Table 1, compositions including gluteraldehyde, didecyl dimethyl ammonium chloride, dodecyl benzyl dimethyl ammonium chloride, ethanol, methyl isothiazolinone, and methyl chloro isothiazolinone provide an effective faster acting biocide, particularly for short exposure times of 1-2 minutes, and even at dilutions 5 and 6 when compared to other biocidal compositions.

In a first aspect, a biocidal fracking fluid additive composition consisting of water, glutaraldehyde in an amount of 0.5% to 35%, alkyl-based quaternary ammonium in an amount of 0.5% to 15%, benzyl-containing quaternary ammonium in an amount of 0.1% to 25%, alcohol in an amount of 0.1% to 10%, an isothiazolinone composition in an amount of 0.0001% to 20%, and magnesium salt in an amount of 0.1% to 20%, wherein the percentages are expressed in weight percent.

In an example of a first aspect, the glutaraldehyde is included in an amount of 10% to 28%. For example, the glutaraldehyde is included in an amount of 15% to 28%, such as an amount of 23% to 28%.

In another example of the first aspect and the above examples, the alkyl-based quaternary ammonium is included in an amount of 5% to 10%. For example, the alkyl-based quaternary ammonium is included in an amount of 6% to 8%.

In a further example of the first aspect and the above examples, the alkyl-based quaternary ammonium includes a dialkyl dimethyl ammonium salt. For example, the dialkyl dimethyl ammonium salt includes an alkyl group having 8 to 18 carbons, such as 8 to 14 carbons or 10 to 12 carbons.

In an additional example of the first aspect and the above examples, the benzyl-containing quaternary ammonium is included in an amount of 2% to 20%. For example, the benzyl-containing quaternary ammonium is included in an amount of 2% to 15%, such as an amount of 3% to 9%.

In another example of the first aspect and the above examples, the benzyl-containing quaternary ammonium includes an alkyl benzyl dialkyl ammonium salt. For example, the alkyl moiety of the alkyl benzyl dialkyl ammonium salt has 8 to 18 carbons, such as 8 to 14 carbons, 8 to 12 carbons, or 10 to 12 carbons. In another example, the dialkyl moiety of the alkyl benzyl dialkyl ammonium salt is a dimethyl or diethyl moiety or a combination thereof. For example, dialkyl moiety of the alkyl benzyl dialkyl ammonium is dimethyl.

In a further example of the first aspect and the above examples, the isothiazolinone composition includes methyl isothiazolinone, methyl chloro isothiazolinone, or a combination thereof.

In an additional example of the first aspect and the above examples, the isothiazolinone composition is included in an amount of 0.0005% to 5%. For example, the isothiazolinone composition is included in an amount of 0.0005% to 1%, such as an amount of 0.001% to 1%.

In another example of the first aspect and the above examples, the alcohol is included in an amount of 0.5% to 5%. For example, the alcohol is included in an amount of 0.5% to 4%, such as an amount of 1.5% to 3%.

In a further example of the first aspect and the above examples, the alcohol is methanol, ethanol, propanol, isopropyl alcohol, or a combination thereof. For example, the alcohol includes ethanol.

In an additional example of the first aspect and the above examples, the magnesium salt includes magnesium chloride, magnesium nitrate, or a combination thereof.

In another example of the first aspect and the above examples, the magnesium salt is included in an amount of 0.5% to 10%. For example, the magnesium salt is included in an amount of 0.5% to 5%.

In a second aspect, a biocide composition includes glutaraldehyde in an amount of 0.5% to 35%, alkyl-based quaternary ammonium in an amount of 0.5% to 15%, benzyl-containing quaternary ammonium in an amount of 0.1% to 25%, and an isothiazolinone composition in an amount of 0.0001% to 20%, wherein the percentages are expressed in weight percent.

In an example of the second aspect, the biocide composition further includes water.

In another example of the second aspect and the above examples, the glutaraldehyde is included in an amount of 10% to 28%. For example, the glutaraldehyde is included in an amount of 15% to 28%, such as an amount of 23% to 28%.

In a further example of the second aspect and the above examples, the alkyl-based quaternary ammonium is included in an amount of 5% to 10%. For example, the alkyl-based quaternary ammonium is included in an amount of 6% to 8%.

In an additional example of the second aspect and the above examples, the alkyl-based quaternary ammonium includes a dialkyl dimethyl ammonium salt.

In another example of the second aspect and the above examples, the dialkyl dimethyl ammonium salt includes an alkyl group having 8 to 18 carbons. For example, the dialkyl dimethyl ammonium salt includes an alkyl group having 8 to 14 carbons, such as 10 to 12 carbons.

In a further example of the second aspect and the above examples, the benzyl-containing quaternary ammonium is included in an amount of 2% to 20%. For example, the benzyl-containing quaternary ammonium is included in an amount of 2% to 15%, such as an amount of 3% to 9%.

In an additional example of the second aspect and the above examples, the benzyl-containing quaternary ammonium includes an alkyl benzyl dialkyl ammonium salt. In an example, the alkyl moiety of the alkyl benzyl dialkyl ammonium salt has 8 to 18 carbons, such as 8 to 14 carbons, 8 to 12 carbons, or 10 to 12 carbons. In another example, the dialkyl moiety of the alkyl benzyl dialkyl ammonium salt is a dimethyl or diethyl moiety or a combination thereof. For example, the dialkyl moiety of the alkyl benzyl dialkyl ammonium is dimethyl.

In another example of the second aspect and the above examples, the isothiazolinone composition includes methyl isothiazolinone, methyl chloro isothiazolinone, or a combination thereof.

In a further example of the second aspect and the above examples, the isothiazolinone composition is included in an amount of 0.0005% to 5%, such as an amount of 0.0005% to 1% or an amount of 0.001% to 1%.

In an additional example of the second aspect and the above examples, the biocide composition includes alcohol in an amount of 0.1% to 10%, such as an amount of 0.5% to 5%, an amount of 0.5% to 4%, or an amount of 1.5% to 3%. In another example of the second aspect and the above examples, the alcohol is methanol, ethanol, propanol, isopropyl alcohol, or a combination thereof. For example, the alcohol includes ethanol.

In another example of the second aspect and the above examples, the biocide composition further includes magnesium salt. For example, the magnesium salt includes magnesium chloride, magnesium nitrate, or a combination thereof. In an example, the magnesium salt is included in an amount of 0.5% to 10%, such as an amount of 0.5% to 5%.

In a third aspect, a biocide composition consists essential of glutaraldehyde in an amount of 0.5% to 35%, alkyl-based quaternary ammonium in an amount of 0.5% to 15%, benzyl-containing quaternary ammonium in an amount of 0.1% to 25%, an isothiazolinone composition in an amount of 0.0001% to 20%, and alcohol in an amount of 0.1% to 10%, wherein the percentages are expressed in weight percent.

In a fourth aspect, a method of treating a well includes flowing a treatment fluid toward a well head and adding a biocide composition to the treatment fluid as it flows toward the well head before it reaches the well head. The biocide composition includes glutaraldehyde in an amount of 0.5% to 35%, alkyl-based quaternary ammonium in an amount of 0.5% to 15%, benzyl-containing quaternary ammonium in an amount of 0.1% to 25%, and an isothiazolinone composition in an amount of 0.0001% to 20%. For example, the treatment fluid includes a fracking fluid.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A biocidal fracking fluid additive composition consisting of:
    water;
    glutaraldehyde in an amount of 0.5% to 35%;
    alkyl-based quaternary ammonium in an amount of 0.5% to 15%;
    benzyl-containing quaternary ammonium in an amount of 0.1% to 25%;

alcohol in an amount of 0.1% to 10%;
an isothiazolinone composition in an amount of 0.0001% to 20%; and
magnesium salt in an amount of 0.1% to 20%;
wherein the percentages are expressed in weight percent.

2. The biocidal fracking fluid additive composition of claim 1, wherein the glutaraldehyde is included in an amount of 10% to 28%.

3. The biocidal fracking fluid additive composition of claim 2, wherein the glutaraldehyde is included in an amount of 15% to 28%.

4. The biocidal fracking fluid additive composition of claim 3, wherein the glutaraldehyde is included in an amount of 23% to 28%.

5. The biocidal fracking fluid additive composition of claim 1, wherein the alkyl-based quaternary ammonium is included in an amount of 5% to 10%.

6. The biocidal fracking fluid additive composition of claim 5, wherein the alkyl-based quaternary ammonium is included in an amount of 6% to 8%.

7. The biocidal fracking fluid additive composition of claim 1, wherein the alkyl-based quaternary ammonium includes a dialkyl dimethyl ammonium salt.

8. The biocidal fracking fluid additive composition of claim 7, wherein the dialkyl dimethyl ammonium salt includes an alkyl group having 8 to 18 carbons.

9. The biocidal fracking fluid additive composition of claim 8, wherein the dialkyl dimethyl ammonium salt includes an alkyl group having 8 to 14 carbons.

10. The biocidal fracking fluid additive composition of claim 1, wherein the benzyl-containing quaternary ammonium is included in an amount of 2% to 20%.

11. The biocidal fracking fluid additive composition of claim 10, wherein the benzyl-containing quaternary ammonium is included in an amount of 2% to 15%.

12. The biocidal fracking fluid additive composition of claim 1, wherein the benzyl-containing quaternary ammonium includes an alkyl benzyl dialkyl ammonium salt.

13. The biocidal fracking fluid additive composition of claim 12, wherein the alkyl moiety of the alkyl benzyl dialkyl ammonium salt has 8 to 18 carbons.

14. The biocidal fracking fluid additive composition of claim 12, wherein the dialkyl moiety of the alkyl benzyl dialkyl ammonium salt is a dimethyl or diethyl moiety or a combination thereof.

15. The biocidal fracking fluid additive composition of claim 14, wherein the dialkyl moiety of the alkyl benzyl dialkyl ammonium salt is dimethyl.

16. The biocidal fracking fluid additive composition of claim 1, wherein the isothiazolinone composition includes methyl isothiazolinone, methyl chloro isothiazolinone, or a combination thereof.

17. The biocidal fracking fluid additive composition of claim 1, wherein the isothiazolinone composition is included in an amount of 0.0005% to 5%.

18. The biocidal fracking fluid additive composition of claim 1, wherein the alcohol is included in an amount of 0.5% to 5%.

19. The biocidal fracking fluid additive composition of claim 1, wherein the alcohol is methanol, ethanol, propanol, isopropyl alcohol, or a combination thereof.

20. The biocidal fracking fluid additive composition of claim 1, wherein the magnesium salt includes magnesium chloride, magnesium nitrate, or a combination thereof.

* * * * *